United States Patent
Hanes, II

(10) Patent No.: US 8,734,319 B2
(45) Date of Patent: May 27, 2014

(54) APPARATUS FOR ORGAN SUSPENSION

(75) Inventor: Charles R. Hanes, II, Mobile, AL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1409 days.

(21) Appl. No.: 12/039,488

(22) Filed: Feb. 28, 2008

(65) Prior Publication Data

US 2008/0207988 A1 Aug. 28, 2008

Related U.S. Application Data

(60) Provisional application No. 60/903,943, filed on Feb. 28, 2007, provisional application No. 60/931,735, filed on May 25, 2007.

(51) Int. Cl.
*A61F 2/00* (2006.01)

(52) U.S. Cl.
USPC .............................. 600/37; 606/139; 606/151

(58) Field of Classification Search
USPC ........ 600/29–32, 37; 606/139, 151–157, 213, 606/215
See application file for complete search history.

(56) References Cited

U.S. PATENT DOCUMENTS

| | | | |
|---|---|---|---|
| 1,222,478 A | 4/1917 | Sheaff | |
| 5,209,754 A | 5/1993 | Ahluwalia | 606/119 |
| 5,304,187 A | 4/1994 | Green et al. | 606/151 |
| 5,354,292 A * | 10/1994 | Braeuer et al. | 606/1 |
| 5,843,108 A | 12/1998 | Samuels | |
| 6,126,594 A | 10/2000 | Bayer | |

(Continued)

FOREIGN PATENT DOCUMENTS

| | | |
|---|---|---|
| WO | WO 96-27332 | 9/1996 |
| WO | WO 02-19946 | 3/2002 |
| WO | WO 02-098301 | 12/2002 |
| WO | WO 2005-110273 | 11/2005 |

OTHER PUBLICATIONS

Barber, et al., "Bilateral Uterosacral Ligament Vaginal Vault Suspension with site-Specific Endopelvic Fascia Defect Repair for Treatment of Pelvic Organ Prolapse", American Journal of Obstetric Gynecology, vol. 183, No. 6, pp. 1402-1411, (Dec. 2000).

(Continued)

*Primary Examiner* — Charles A Marmor, II
*Assistant Examiner* — Carrie R Dorna

(57) ABSTRACT

Disclosed herein are a number of embodiments of methods for suspending an organ in a body, and many embodiments of apparatus for suspending an organ in a body. One embodiment provides an apparatus comprising a sleeve having a lumen. A dissecting instrument is slidably located within the lumen. The dissecting instrument includes a channel useful for hydrodissection. An operating instrument is slidably located within the lumen. The operating instrument includes a graft chamber for conveying a graft for fixation between the organ and the body. The operating instrument includes at least one operating channel that accepts a fixation device that fixes the graft between the organ and the body. In one method, an incision is made in the body. An operating instrument bearing a graft is inserted into a sleeve. The sleeve and the operating instrument are inserted through the incision. A fixation device is inserted into the operating instrument. The graft is fixed to the body with the fixation device. The fixation device is removed from the operating instrument. The operating device and the sleeve are removed through the incision. The graft is attached to the organ.

30 Claims, 7 Drawing Sheets

(56) References Cited

U.S. PATENT DOCUMENTS

| | | | |
|---|---|---|---|
| 6,235,037 B1 | 5/2001 | East et al. | 606/119 |
| 6,315,713 B1 | 11/2001 | Takada | |
| 6,319,272 B1 | 11/2001 | Brenneman et al. | 606/232 |
| 6,364,832 B1 | 4/2002 | Propp | |
| 6,423,075 B1 | 7/2002 | Singh et al. | 606/119 |
| 6,572,631 B1 | 6/2003 | McCartney | 606/167 |
| 6,592,515 B2 | 7/2003 | Thierfelder et al. | 600/37 |
| 6,755,781 B2 | 6/2004 | Gellman | 600/38 |
| 6,884,212 B2 | 4/2005 | Thierfelder et al. | 600/30 |
| 6,936,052 B2 | 8/2005 | Gellman et al. | 606/99 |
| 6,953,428 B2 | 10/2005 | Gellman et al. | 600/29 |
| 6,991,597 B2 | 1/2006 | Gellman et al. | 600/37 |
| 7,025,063 B2 | 4/2006 | Snitkin et al. | 128/885 |
| 7,025,772 B2 | 4/2006 | Gellman et al. | 606/151 |
| 7,070,558 B2 | 7/2006 | Gellman et al. | 600/37 |
| 7,235,043 B2 | 6/2007 | Gellman et al. | 600/29 |
| 7,867,222 B1 * | 1/2011 | Tilton et al. | 606/1 |
| 7,874,982 B2 | 1/2011 | Selover | |
| 2002/0028980 A1 | 3/2002 | Thierfelder et al. | 600/37 |
| 2002/0123668 A1 | 9/2002 | Ritland | |
| 2003/0236447 A1 | 12/2003 | Ritland | |
| 2004/0230092 A1 | 11/2004 | Thierfelder et al. | 600/37 |
| 2005/0065395 A1 | 3/2005 | Mellier | 600/37 |
| 2005/0107805 A1 | 5/2005 | Bouffier et al. | |
| 2005/0216013 A1 | 9/2005 | Dallara | |
| 2006/0173483 A1 | 8/2006 | Kieturakis et al. | |
| 2006/0212046 A1 | 9/2006 | Pearce | |
| 2006/0260618 A1 | 11/2006 | Hodroff et al. | 128/830 |
| 2007/0219416 A1 | 9/2007 | Perez-Cruet | |
| 2008/0275306 A1 | 11/2008 | Rebuffat | |
| 2009/0099422 A1 | 4/2009 | George | |
| 2011/0208226 A1 | 8/2011 | Fatone | |

OTHER PUBLICATIONS

Benson, et al., "Vaginal Versus Abdominal Recontructive Surgery for the Treatment of Pelvic Support Defects: A Prospective Randomized Study with Long-Term Outcome Evaluation", American Journal of Obstetric Gynecology, vol. 175, pp. 1418-1422, (Dec. 1996).

Cundiff, et al., "Abdominal Sacral Colpoperineopexy: A New Approach for Correction of Posterior Compartment Defects and Perineal Descent Associated with Vaginal Vault Prolapse", American Journal of Obstetric Gynecology, vol. 177, No. 6, pp. 1345-1355, (Dec. 1997).

Elliott, et al., "Long-Term Results of Robotic Assisted Laparoscopic Sacrocolpopexy for the Treatment of High Grade Vaginal Vault Prolapse", Journal of Urology, vol. 176, No. 2, pp. 655-659, (Aug. 2006) Abstract Only.

Karram, et al., "High Uterosacral Vaginal Vault Suspension with Fascial Reconstruction for Vaginal Repair of Enterocele and Vaginal Vault Prolapse", American Journal of Obstetric Gynecology, vol. 185, No. 6, pp. 1339-1343, (Dec. 2001).

Maher, et al., "Abdominal Sacral Colpopexy or Vaginal Acrospinous Colpopexy for Vaginal Vault Prolapse: A Prospective Randomized Study", American Journal of Obstetric Gynecology, vol. 190, pp. 20-26 (2004).

Morley, et al., "Sacrospinous Ligament Fixation for Eversion of the Vagina", American Journal of Obstetric Gynecology, vol. 158, No. 5, pp. 872-881, (Apr. 1988) Abstract Only.

Nezhat, et al., "Robotic-Assisted Laparoscopy in Gynecological Surgery", Journal of the Society of Laparoendoscopic Surgeons, vol. 10, No. 3, pp. 317-320, (2006).

Nygaard, et al., "Abdominal Sacrocolpopexy: A Comprehensive Review", Obstetricians and Gynecologists, vol. 104, No. 4, pp. 805-823, (Oct. 2004).

JW Ross, "Techniques of Laparoscopic Repair of Total Vault Eversion After Hysterectomy", Journal of the American Association of Gynecological Laparoscopy, vol. 4, No. 2, pp. 173-183, (Feb. 1997) Abstract Only.

Shull, at al., "A Transvaginal Approach to Repair of Apical and Other Associated Sites of Pelvic Organ Prolapse with Uterosacral Ligaments", American Journal of Obstetric Gynecology, vol. 183, No. 6, pp. 1365-1374 (Dec. 2000).

Silva, et al., "Uterosacral Ligament Vault Suspension: Five-Year Outcomes", Obstetrics and Gynecology, vol. 108, No. 2, pp. 255-263, (Aug. 2006).

Su, et al., "Abdominovaginal Sacral Colpoperiheopexy: A Quality of Life Assessment", Journal of Pelvic Medicine & Surgery, vol. 13, No. 4, pp. 181-190, (Aug./Sep. 2007).

Sze, et al., "Transvaginal Repair of Vault Prolapse: A Review", Obstetrics & Gynecology, vol. 89, No. 3, pp. 466-475, (Mar. 1997).

Van der Weiden, et al., "A New Device for Bone Anchor Fixation in Laparoscopic Sacrocolpopexy: The Franciscan Laparoscopic Bone Anchor Inserter", Surgical Endoscopy, vol. 19, pp. 594-597, (2005).

Visco, et al., "Vaginal Mesh Erosion After Abdominal Sacral Colpopexy", American Journal of Obstetric Gynecology, vol. 184, pp. 297-302 (Feb. 2001).

Prolele and Merilene, Description of products: polyethylene mesh Prolene and polyester mesh Mersilene, Medcompare—The Buyer's Guide for Medical Professionals, http://www.medcompare.com/details/358621/prolene-polypropylene (Jun. 25, 2008).

ProTrak 5 mm (Single Use Instrument), Description of product: ProTrak 5 mm (Single Use Instrument), Autosuture—Advancing Possibilities in Surgery, http:www.autosuture.com (Jun. 25, 2008).

Hall, et al., "Laparoscopic Sacrocolpopexy: Lessons Learned", Journal of Pelvic Medicine & Surgery, vol. 13, No. 4, pp. 197-201, (Jul./Aug. 2007).

Flynn, et al., "Abdominal Surgery for Pelvic Organ Prolapse", Journal of Pelvic Medicine & Surgery, vol. 13, No. 4, pp. 157-170, (Jul./Aug. 2007).

International Search Report, pp. 1-4 (Aug. 15, 2008).

Non-Final Office Action for U.S. Appl. No. 12/760,055, mailed Jun. 15, 2012, 15 pages.

Non-Final Office Action Response for U.S. Appl. No. 12/760,055, filed Sep. 10, 2012, 7 pages.

Final Office Action for U.S. Appl. No. 12/760,055, mailed Nov. 23, 2012, 17 pages.

First Examiners Report for Australian Application No. 2008221334, mailed Jul. 19, 2012, 3 pages.

Final Office Action for U.S. Appl. No. 12/760,055, mailed Nov. 23, 2012, 15 pages.

Final Office Action Response and RCE for U.S. Appl. No. 12/760,055, filed Feb. 22, 2013, 10 pages.

Non-Final Office Action for U.S. Appl. No. 12/760,055, mailed Oct. 8, 2013, 14 pages.

* cited by examiner

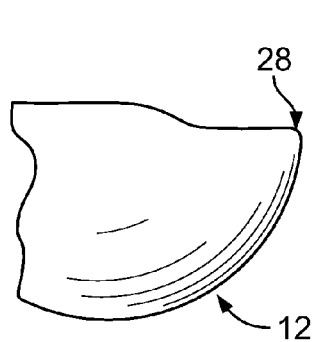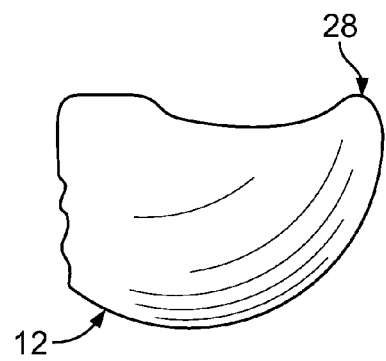
FIG. 7A  FIG. 7B
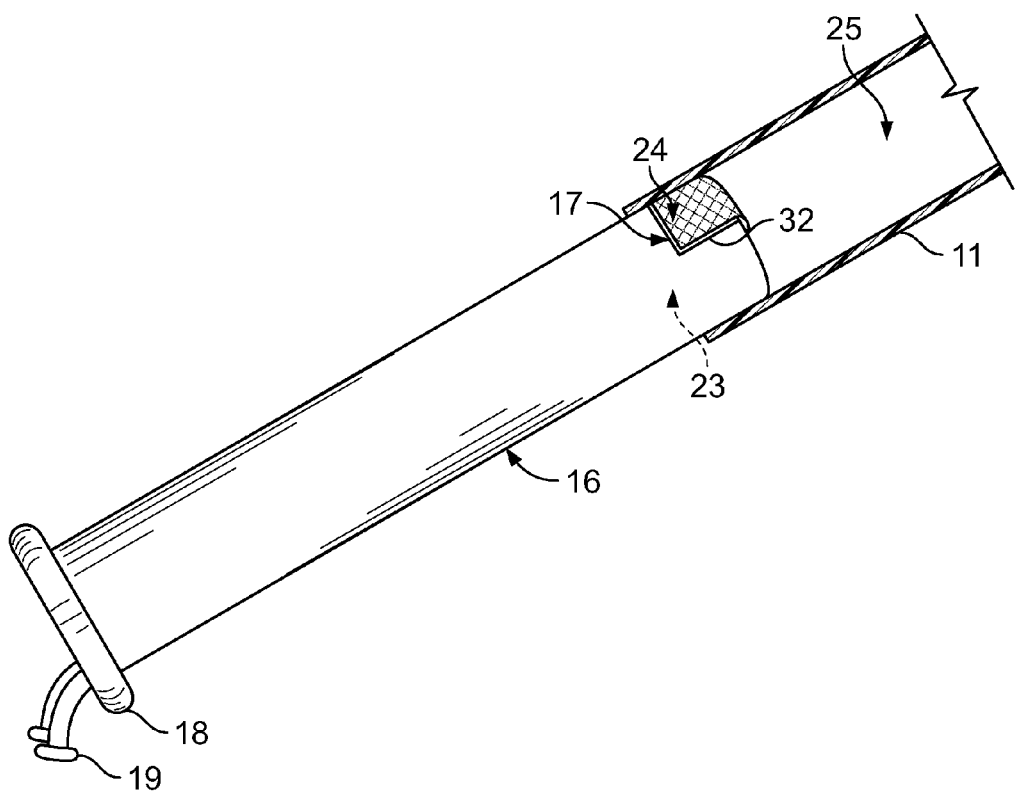
FIG. 8

APPARATUS FOR ORGAN SUSPENSION

REFERENCE TO RELATED APPLICATIONS

This patent application claims priority from U.S. Provisional Patent Application No. 60/903,943 filed on Feb. 28, 2007 and U.S. Provisional Patent Application No. 60/931,735 filed on May 25, 2007.

BACKGROUND

Embodiments described herein generally relate to an apparatus and a method for suspending an organ, a tissue, or other part of a body, such as a human body. More specifically, to correct organ prolapse, such as vaginal vault prolapse, the embodiments described herein enable a vaginal sacral colpopexy operation performed by a transvaginal approach which substantially reduces the need to invade the intraperitoneal space.

Abdominal sacral colpopexy (ASC) is widely recognized as the "gold standard" of all operations to restore vaginal suspension. Traditionally, sacral colpopexy has been performed through an abdominal incision. There are some accomplished laparoscopic surgeons who are able to do this procedure laparoscopically, however, doing this may be difficult for many surgeons. With the introduction of a robot in laparoscopic surgery, these surgical procedures may become more commonplace. However, use of a robot is rather expensive and may be time consuming.

There are a large number of surgeons that advocate vaginal surgery using a growing number of surgical procedures and devices that suspend the vagina to the uterosacral or sacrospinous ligaments. The advantage of these procedures is that vaginal surgery, in general, is easier for the patient to recover from and often has lower operative morbidity than the abdominal operations.

If a sacral colpopexy operation can be performed using a transvaginal technique that does not deviate from the optimal abdominal technique, then advantages of being able to offer the gold standard operation will be enhanced by avoiding unattractive aspects of abdominal surgery. In addition, if a sacral colpopexy operation can be done in a fashion that is technically safe and easy, then many surgeons may incorporate a sacral colpopexy into their standard practice.

One of the technical challenges of a vaginal sacral colpopexy is creating a correct operative plane between the vagina and bladder anteriorly and between the vagina and rectum posteriorly. With recent vaginal techniques using graft material, these operative planes are created through vaginal incisions with the aid of hydrodissection. These planes are exactly the same as the operative planes used with ASC. The operative planes extend from the site of the vaginal incision up to and around the top of the vagina. From this point, there is only a distance of about 5 to about 10 centimeters to the sacral promontory. Normally, sacral fixation points of ASC are in the body or the presacral fascia overlying the body of the vertebra at or just below the sacral promontory.

The sacral fixation points may be safely accessed with appropriate operating instruments that are passed into and through the vagina. A suspension graft may be attached at the identical sites where they would be attached using the standard ASC procedure, while avoiding invading the sacral blood vessels. In addition, installation of the graft may be accomplished more quickly with trans-vaginal sacral colpopexy than with ASC. While embodiments described herein do not specify the type of graft material to be used, it is anticipated that, in keeping with the goal of duplicating the ASC standard abdominal technique, a permanent synthetic mesh graft will be used. However, embodiments described here are not limited to this graft material and may be used to apply any type of biocompatible graft material having properties suitable for organ suspension.

SUMMARY

Disclosed herein are a number of embodiments of methods for suspending an organ in a body, and many embodiments of apparatus for suspending an organ in a body. One embodiment provides an apparatus comprising a sleeve having at least one lumen. A dissecting instrument is slidably located within the lumen. The dissecting instrument includes a working channel useful for performing hydrodissection for separating the organ and its surrounding fascia. An operating instrument is slidably located within the at least one lumen of the sleeve. The operating instrument includes a graft chamber for conveying a graft for fixation between the organ and the body. The operating instrument includes at least one working channel that accepts a fixation device that fixes the graft between the organ and the body.

According to another embodiment, a method of suspending a vagina from a sacrum comprises the steps of making an incision through the vaginal wall followed by dissection through the retroperitoneal space between the vagina and rectum to access the sacral promontory. An apparatus comprising a lumen for introduction of an identifier to identify blood vessels, a graft chamber conveying a graft, and a lumen for introducing a fixation device, is inserted through the vaginal incision and dissected space. The sacral blood vessels are identified with the identifier, which may comprise an optical endoscope or an ultrasound probe, or similar device to facilitate viewing or imaging the sacral space and aiding in identifying the sacral blood vessels. A fixation site on the sacral promontory is selected with the aid of the identifier and a distal end of the graft is affixed to the sacral fixation. The graft is removed or released from the graft chamber after the graft is fixed at the fixation site with the fixation device. The apparatus is then removed through the vaginal incision and the proximal end or ends of the graft are affixed, such as by suturing, to the vaginal wall. It will be understood by those skilled in the art that the proximal affixation of the graft to the vagina will oftentimes occur at the vaginal apex, but it may also be necessary to affix the graft to the lateral, posterior and/or anterior walls of the vagina to obtain desired suspension of the vagina.

A further embodiment provides a method of suspending an organ in a body. In this method, a small incision is made in the body to access the desired anatomical space. A dissecting instrument is inserted into a lumen in an introducer sleeve. The introducer sleeve and the dissecting instrument are inserted through the incision and into the desired anatomical space. Internal dissection is made to access a desired fixation location within the body and the dissection instrument is removed from the lumen in the introducer sleeve. An operating instrument bearing a graft is inserted into the lumen in the introducer sleeve and passed to the desired fixation position in the body. A fixation device is inserted into the operating instrument or into the introducer sleeve and passed to the fixation point. The graft is fixed to the fixation location using the fixation device to secure one end of the graft to the fixation point and the fixation device removed from the body. The operating device and the sleeve are then withdrawn through the incision to release the graft and the other end of the graft is secured to the organ requiring suspension.

An additional method is provided by another embodiment. In this method, an incision is made in the body. An operating instrument bearing a graft is inserted into a sleeve. The sleeve and the operating instrument are inserted through the incision. A fixation device is inserted into the operating instrument. The graft is fixed to the body with the fixation device. The fixation device is removed from the operating instrument. The operating device and the sleeve are removed through the incision. The graft is attached to the organ.

Yet another embodiment provides an apparatus for suspending an organ within a body. This comprises a sleeve having a lumen. An operating instrument is slidably located within the lumen. The operating instrument includes a graft chamber for conveying a graft for fixation between the organ and the body. The operating instrument includes at least one operating channel accepting a fixation device that fixes the graft between the organ and the body.

BRIEF DESCRIPTION OF THE DRAWINGS

FIG. 7A is an elevational view an embodiment of a distal tip of the dissecting instrument of FIG. 3;

FIG. 7B is an elevational view another embodiment of a distal tip of the dissecting instrument of FIG. 3;

FIG. 8 is a partially sectioned, perspective view of the operating instrument described herein with a graft being inserted into a sleeve;

DETAILED DESCRIPTION

Described herein are a number of embodiments of apparatus and methods that generally relate to suspending an organ, a tissue, or other part of a body, such as a human body. More specifically, these embodiments enable a vaginal sacral colpopexy operation performed by a transvaginal approach. While the embodiments are discussed herein with respect to vaginal suspension to correct vaginal prolapse, this reference is exemplary only and intended to aid understanding, it is to be recognized that the embodiments can be used to suspend any body organ. It is to be understood that elements of the various embodiments and steps of various methods may be combined in any appropriate fashion to meet requirements of a particular application or operator, such as a doctor and the like, using the apparatus and/or methods. While general construction of the apparatus is described below, it is to be understood that aspects of the construction may become clearer upon careful consideration of the methods of using the apparatus.

Figure 1:
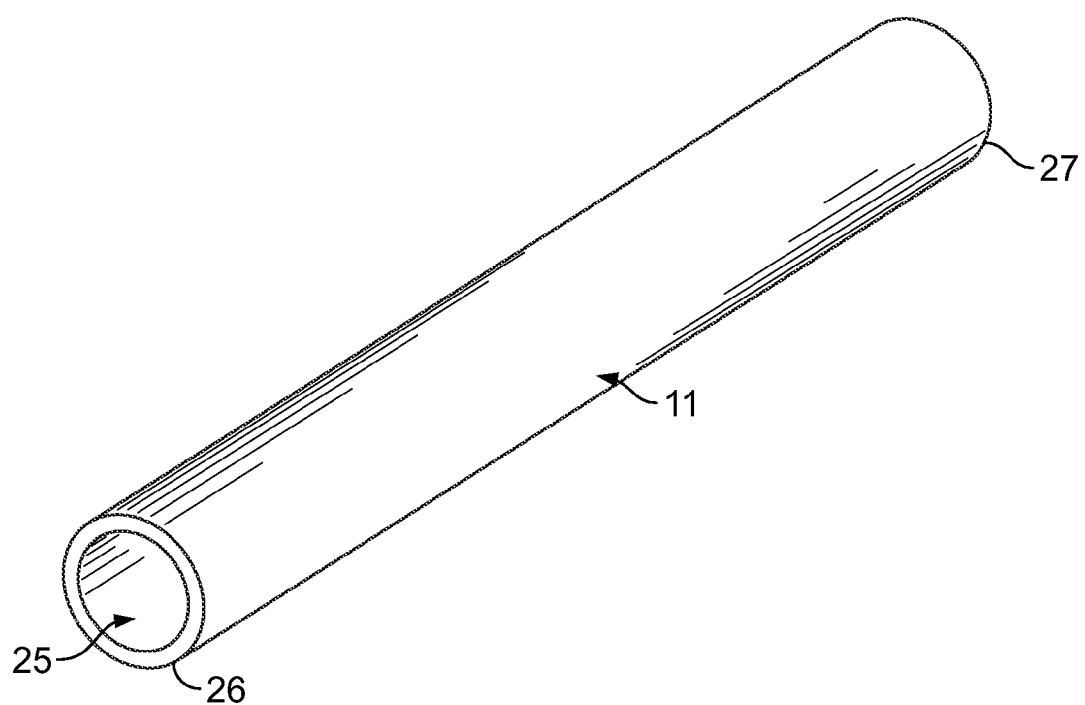
FIG. 1 is a perspective view of an introducer sleeve as described herein.
Figure 2:
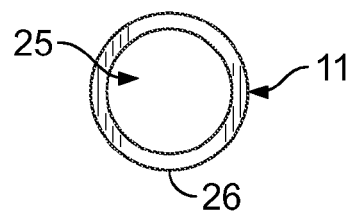
FIG. 2 is an end view of the introducer sleeve of FIG. 1.

FIGS. 1 and 2 show an introducer sleeve 11. The introducer sleeve 11 has a substantially hollow, tube-like structure. Introducer sleeve 11 includes a lumen 25 that extends through the introducer sleeve 11 between a proximal end 26 and a distal end 27 of the introducer sleeve 11 and is open at a distal end 27 thereof. A dissecting instrument 12 and an operating instrument 16, at appropriate times, may be slidably located in the lumen 25 in the introducer sleeve 11. Opposite ends of the introducer sleeve 11 are open to allow items to pass freely through the introducer sleeve 11. The introducer sleeve 11 may have a transverse cross section of any suitable shape, such as elliptical (shown in FIG. 9), circular or any combination of these shapes at various locations along an axial length of the introducer sleeve 11. The introducer sleeve 11 should have a length sufficient to span an anatomical distance between a vaginal incision and the sacral promontory. Preferably, the introducer sleeve 11 is about 20 cm long and has an inner diameter measuring substantially within the range of about 1.5 cm to about 3 cm. While the introducer sleeve 11 is shown in the Figures as being substantially cylindrical, in some embodiments, the introducer sleeve 11 may be provided with a structure, such as a handle, a gripping surface or the like to facilitate manipulation of the introducer sleeve 11.

Figure 3:
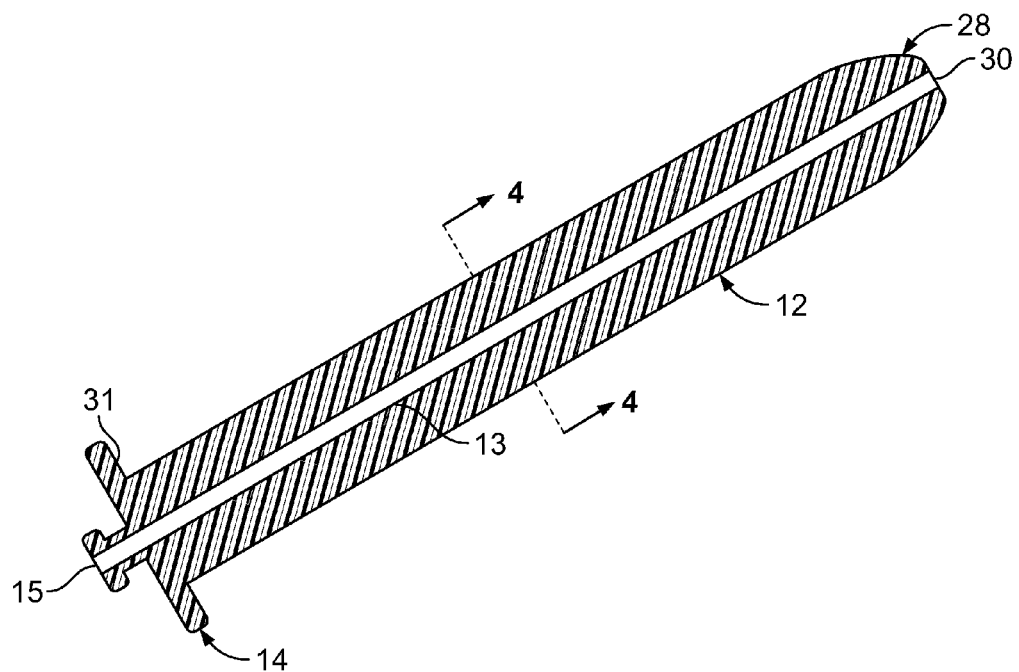
FIG. 3 is a sectioned perspective view of a dissecting instrument described herein.
Figure 4:
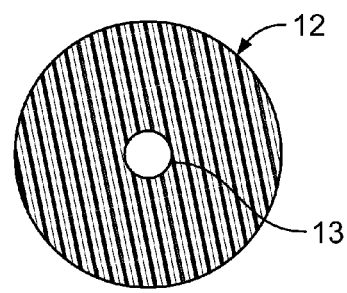
FIG. 4 is a sectional view taken along line 4-4 of FIG. 3.

One embodiment of the dissecting instrument 12 is shown in FIGS. 3 and 4. Dissecting instrument 12 also has a generally elongate tubular configuration configured to fit moveably within the lumen 27 of the introducer sleeve. A distal end 28 of the dissecting instrument 12 may have a substantially blunt or rounded configuration, as shown in FIG. 3, or may have a substantially tapered, pointed or other configuration, as shown in FIGS. 7A and 7B. The distal end 28 of the dissecting instrument 12 may have any suitable configuration as long as the distal end 28 fits in the lumen 25 of the introducer sleeve 11. Preferably, the configuration of the distal end 28 is chosen to facilitate dissection. When inserted in and advanced an appropriate distance through the lumen 25 of the introducer sleeve 11, the distal end 28 of the dissecting instrument 12 extends beyond the distal end 27 (the end that is inserted through the incision and will be advanced into close proximity with the sacrum) of the introducer sleeve 11.

The dissecting instrument 12 has a channel 13 that extends a longitudinal length of the dissecting instrument 12. The channel 13 has a proximal end and a distal end. The distal end of the channel 13 terminates at a port 30. The port 30 may be located adjacent a center of the distal end of the dissecting instrument 12, may be located adjacent an edge of the distal end of the dissecting instrument 12 or may be located at any suitable location there between. The proximal end of the channel 13 terminates at a connector 15, such as a Luer lock and the like, that permits connection of a source of suitable fluid to the channel 13. Thus, the channel 13 may be used for any appropriate purpose, such as irrigation, hydrodissection or the like. If the channel 13 is used for hydrodissection, hydrodissection can take place as the dissecting instrument 12 is moved through a vaginal incision and advanced toward the sacrum in the retroperitoneal space. A suitable controller may be provided, mounted with the source of suitable fluid or with the dissecting instrument 12, and is operatively associated with the channel 13 to control flow of fluid in the channel 13. The dissecting instrument 12 may have a second channel extending along a longitudinal length of the dissecting instrument 12, and this second channel maybe used for any appropriate purpose, such as suction and the like. A flange 14 is disposed at the proximal end of the dissecting instrument 12.

The flange 14 has a surface 31 that is engageable with the proximal end 26 of the introducer sleeve 11 to restrict longitudinal movement of the dissecting instrument 12 through the lumen 25 of the introducer sleeve 11. In this manner, longitudinal movement of the dissecting instrument 12 through the lumen 25 is restricted. In a preferred embodiment, a distance between the surface 31 of the flange 14 and the distal end 28 of the dissecting instrument 12 is about 20 cm.

Figure 5A:
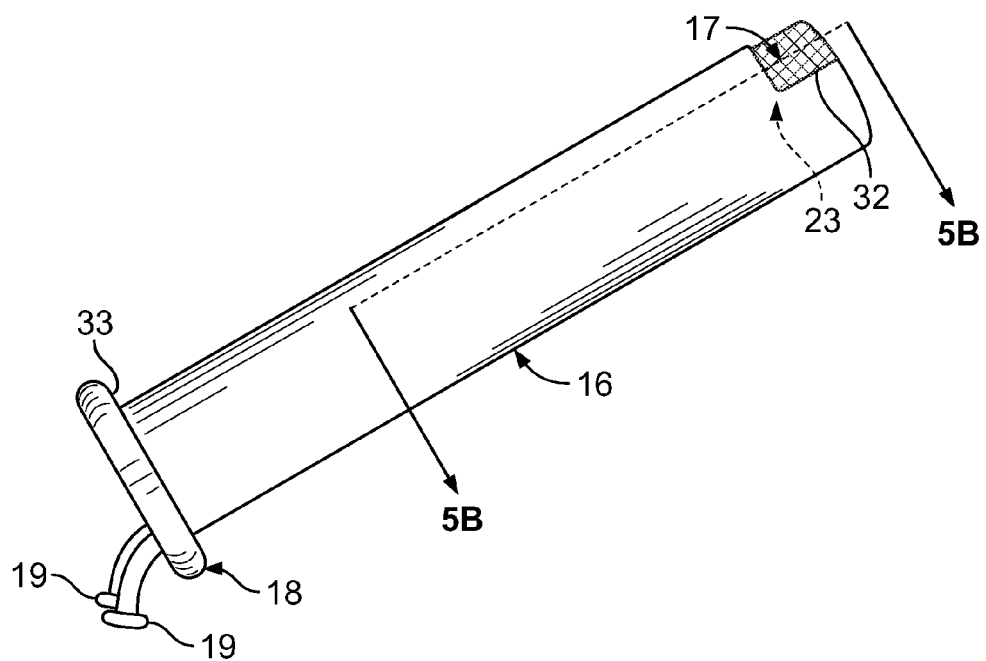
FIG. 5A is a perspective view of an operating instrument described herein.
Figure 5B:
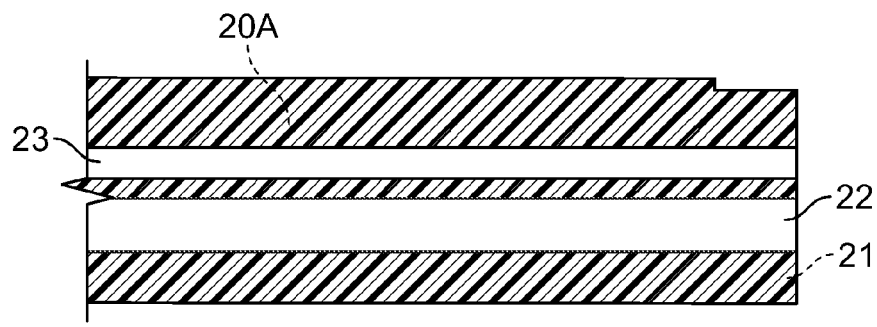
FIG. 5B is a cross-sectional view taken along line 5B-5B of FIG. 5A.

FIGS. 5A and 5B illustrate an embodiment of an operating instrument 16. The operating instrument 16 has a cross-sectional shape identical to that of the dissecting instrument 12 as the operating instrument 16 also is intended to be inserted into the lumen 25 in the introducer sleeve 11. In one embodiment, the operating instrument 16 is substantially cylindrical. In some embodiments, the operating instrument 16 includes a recess 17, shown in FIGS. 5A, 5B, 6A, 6B and 8, adjacent a distal end of the operating instrument 16. The recess 17 is configured to accept a portion, i.e. the sacral portion, of a graft 24 for suspending the vagina from the sacrum. The graft 24 may be of any suitable material and construction, such as the construction of grafts that are currently available, such as, for example, polyethylene mesh (PROLENE, Ethicon, Inc.) or polyester mesh (MERSILINE, Ethicon, Inc.). The graft 24 may be suitably manipulated, such as pleated, folded, rolled or the like, to facilitate placement of the graft 24 in a graft chamber 23 in the operating instrument 15 and removal of the graft 24 from the graft chamber 23 during installation of the graft 24 during an operation. The graft chamber 23 suitably conveys the graft 24 to a position where the graft 24 may be fixed as desired.

In some embodiments, an outer diameter of the operating instrument 16 measures substantially within the range of about 1.5 cm to about 3 cm. The recess 17 includes a graft supporting platform 32 that recedes from the outer diameter of the operating instrument 16 by a distance that is substantially equivalent to a thickness of the graft 24. Preferably, this distance measures substantially within the range of about 0.5 mm to about 0.25 mm. The graft 24 extends from a graft chamber 23 disposed within the operating instrument 16 across a distal end of the operating instrument 16 to the recess 17. The graft chamber 23 is configured and has dimensions sufficient to carry at least a portion of the graft 24. As the inner diameter of the introducer sleeve 11 and outer diameter of the operating instrument 16 both measure substantially within the range of about 1.5 cm to about 3 cm, the operating instrument 16 fits relatively tightly within the lumen 25. This relatively tight fit of the operating instrument 16 within the lumen 25 insures that the portion of the graft 24 disposed on the graft supporting platform 32 remains on the graft supporting platform 32 until the graft 24 is fixed to the sacrum.

In some embodiments, the operating instrument 16 does not have a recess 17 or a graft supporting platform 32. In these embodiments, the graft 24 is disposed in the graft chamber 23 and a sacral portion of the graft 24 is extended over the distal end of the operating instrument 16. Clearance between an inner diameter surface of the introducer sleeve 11 and an outer diameter surface of the operating instrument 16 is substantially equal to a width of the graft 24. Generally, the introducer sleeve 11, the dissecting instrument 12 and the operating instrument 16 have substantially similarly shaped latitudinal cross sections. These configurations facilitate longitudinal movement of either the dissecting instrument 12 or the operating instrument 16 through the lumen 25 of the introducer sleeve 11.

Figure 9:
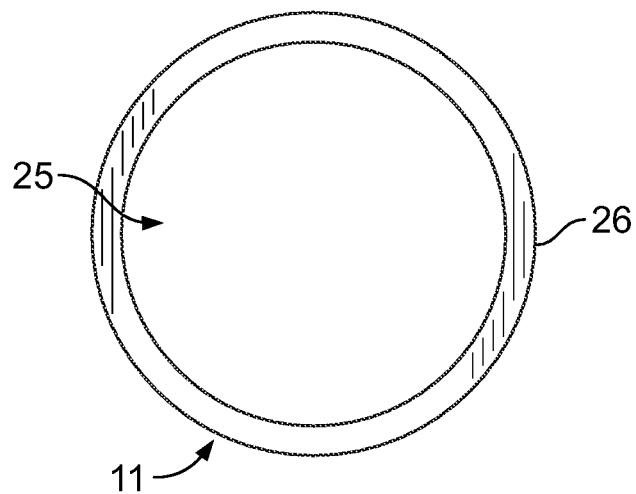
FIG. 9 is a distal end view of an embodiment of the introducer sleeve described herein.
Figure 10:
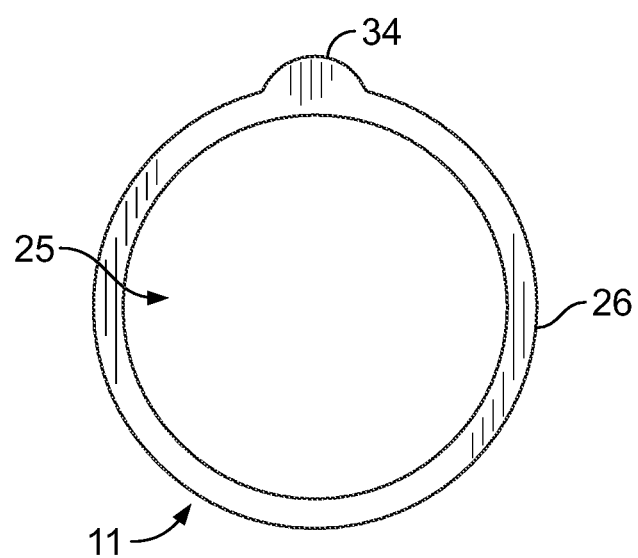
FIG. 10 is a distal end view of an embodiment of the introducer sleeve described herein.

In other embodiments, the introducer sleeve 11 may have a substantially elliptical configuration, as shown in FIG. 9, or may be provided with a pocket 34 that accommodates the graft 24. If provided, the pocket 34 defines a space sufficient to accept a portion of the graft 24 that may be disposed on the outer surface of the operating instrument 16. In any embodiment, clearance between an inner diameter of the introducer sleeve 11 and an outer diameter of the operating instrument 16 is appropriate to retain the graft 24 in proper position on the operating instrument 16 during insertion of the operating instrument through the lumen 25 and subsequent fixation of the graft 24.

Figure 11:
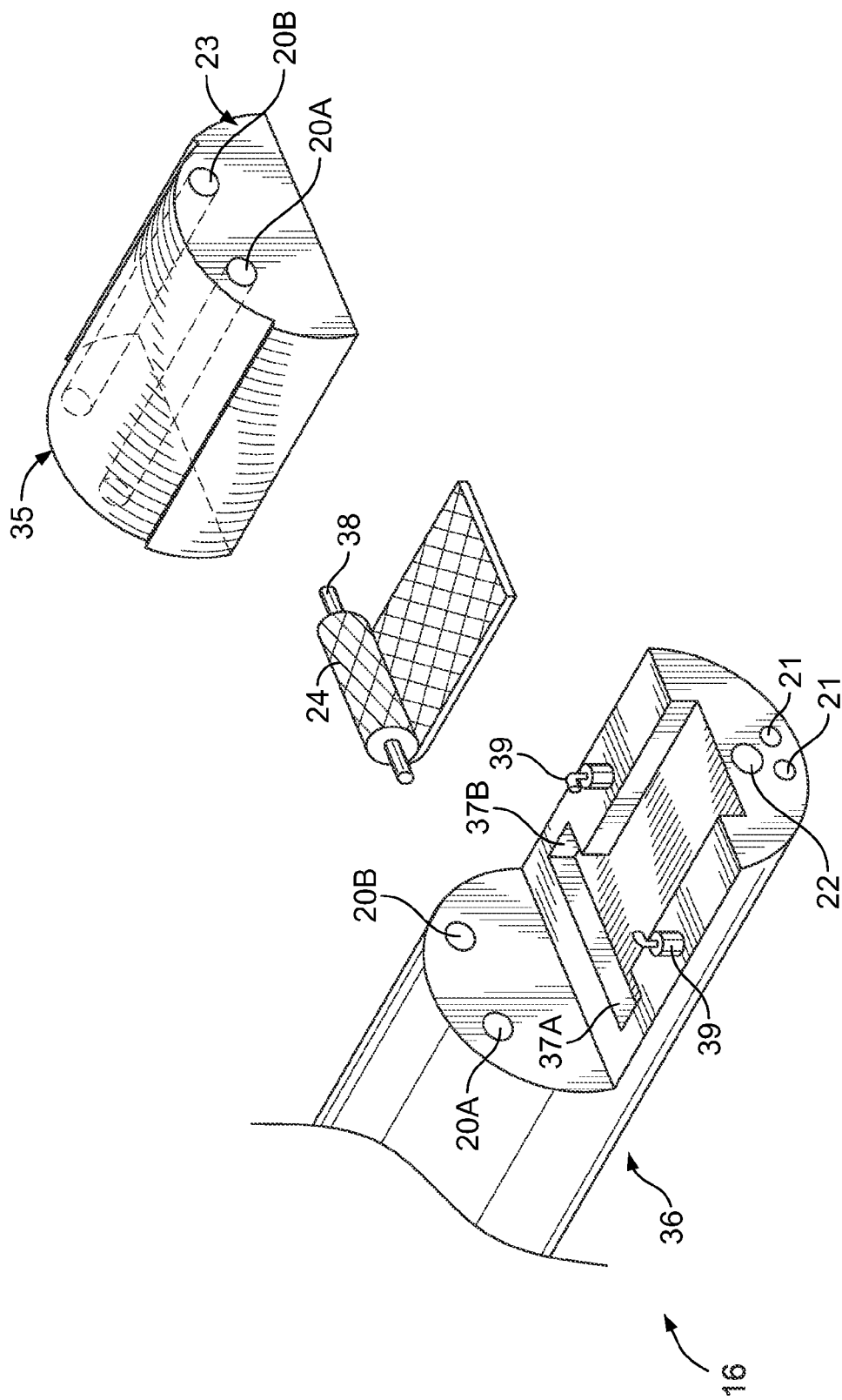
FIG. 11 is an exploded view of an embodiment of an operating instrument described herein.

In other embodiments, irrespective of whether the operating instrument 16 has a recess 17 or a graft support platform 32 or not, the operating instrument 16 may include a separable portion 35, as shown in FIG. 11. The separable portion 35 is disposed at a distal end of the operating instrument 16. The separable portion 35 can be removably attached to a main body 36 of the operating instrument 16 by any suitable means, such as a hinge, or other items that provide a slidable fit between the separable portion 35 and the main body 36. Removal of the separable portion 35 facilitates access to the graft chamber 23. The separable portion 35 can include a portion of the graft chamber 23 and portions of operating channels 20A and 20B.

In some embodiments, the main body 36 includes at least one mount (a pair of mounts 37A and 37B are shown in FIG. 11 for clarity), such as projections, slots or the like, that rotatably bears a rod 38 upon which the graft 24 is disposed. The graft 24 can be suitably oriented, such as folded, wrapped and/or wound, on the rod 38 so that the rod 38 can rotate and the graft 24 can move off of the rod 38 during fixation of the graft 24 to the sacrum. At least one member (a pair of members 39 is shown in FIG. 11) is located on the main body 36 spaced distally of the mounts 37A and 37B to suitably adjust movement, i.e. unfold, separate or the like, of the graft 24 as the graft 24 moves off of the rod 38 during fixation of the graft 24.

The separable portion 35 can be removed from the main body 36 to facilitate application of the graft 24 to the graft chamber 23. The graft 24 can be placed within the graft chamber 23, or, if included in the particular embodiment used, the rod 38 bearing the graft 24 can be installed on the features 37A and 37B. Upon application of the graft 24 to the graft chamber 23, the separable portion 35 can be applied to the main body 36 of the operating instrument 16. In one embodiment, the separable portion 35 is moved or is slid onto the main body 36. In another embodiment, the separable portion 35 is hingedly connected to the main body 36 so that the separable portion can move between an open position where graft 24 is added to the graft chamber 23 and a closed position where the operating instrument 16 is ready for insertion into the lumen 25.

A proximal end of the operating instrument 16 includes a flange 18 constructed similarly to the flange 14 on the dissecting instrument 12. The flange 18 has a surface 33 that is engageable with the proximal end 26 of the introducer sleeve 11 to restrict longitudinal movement of the operating instrument 16 through the lumen 25 of the introducer sleeve 11. In this manner, longitudinal movement of the operating instrument 16 through the lumen 25 is limited. The operating instrument 16 must be long enough to extend from a location of contact between the surface 33 of the flange 18 and the introducer sleeve 11 to the sacrum. In a preferred embodiment, a distance between the surface 33 of the flange 18 and the distal end of the operating instrument 16 is about 20 cm.

The operating instrument 16 includes at least one operating channel that extends from the flange 18 to the distal end of the operating instrument 16. In the embodiment illustrated in FIGS. 6A and 6B, there are two operating channels 20A and 20B. There may be any desired number of operating channels 20A and 20B disposed on the operating instrument 16 and the operating channels 20A and 20B may be positioned at any suitable location on the operating instrument 16. In the embodiment of FIG. 6C, the two operating channels 20A and 20B are replaced by a single operating channel 20C. The operating channel 20C has a substantially elliptical latitudinal cross section. Lateral ends of the operating channel 20C are positioned on the operating instrument 16 at substantially the same position of lateral ends of the operating channels 20A and 20B. The operating channel 20C permits lateral movement of a fixation device within the operating channel 20C to provide increased flexibility during fixation of the graft 24. In a preferred embodiment, each of the operating channels 20A and 20B are constructed to accept appropriate fixation devices, such as the ProTack™ 5 mm (Single Use Instrument) available from United States Surgical, a business unit of Tyco Healthcare. Other fixation devices can be used with the operating instrument 16 with suitable modification to the operating channels 20A and 20B to accommodate the fixation devices. Also, one operating channel 20A may be constructed to use with one fixation device and the other operating channel 20B may be constructed for use with another, different fixation device.

Figures 6A, 6B:
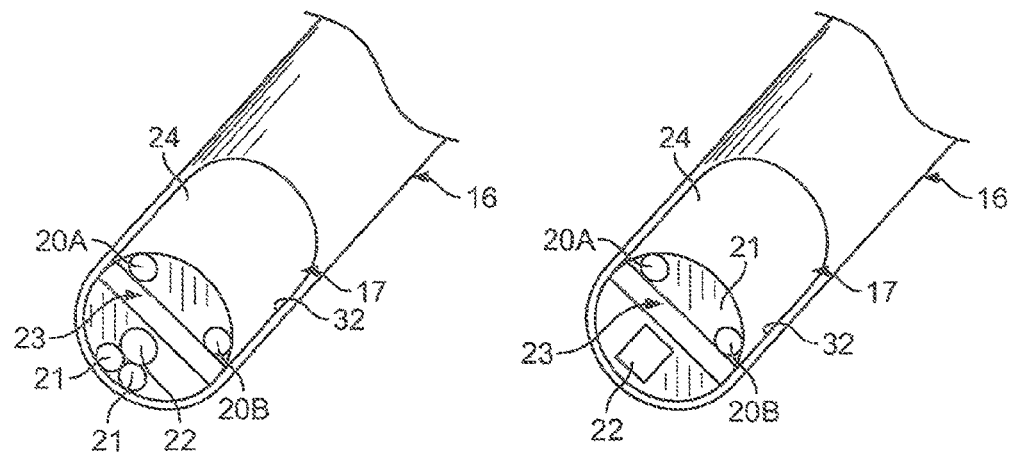
FIG. 6A is a perspective view of an embodiment of a distal end of the operating instrument of FIG. 5.
FIG. 6B is a perspective view of a distal end of another embodiment of the operating instrument of FIG. 5.
Figure 6C:
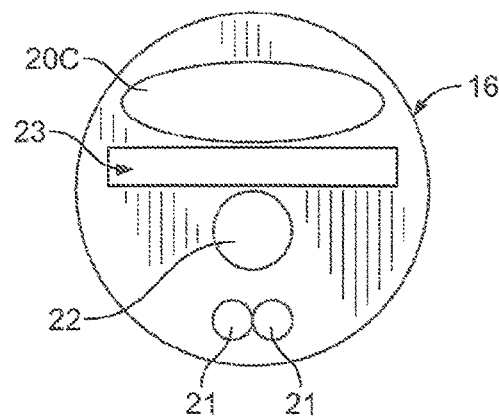
FIG. 6C is an end view of another embodiment of the operating instrument of FIG. 5.

FIG. 6A shows a distal end of one embodiment of the operating instrument 16. In this embodiment, there are five channels that pass through an axial length of the operating instrument 16. The two operating channels 20A and 20B are located adjacent an outer edge of the operating instrument 16 between the graft chamber 23 and the graft supporting platform 32. With this orientation, a majority of the graft 24 can be disposed in the graft chamber 23 and a sacral end of the graft 24 can be disposed on the graft supporting platform 32. In this manner, a portion of the graft, not shown for clarity in FIGS. 6A and 6B, extends in front of distal ends of the operating channels 20A and 20B. This arrangement facilitates fixation of the graft 24 to the sacrum by fixation devices.

In some embodiments, there are additional channels disposed on the operating instrument 16. A substantially central channel 22 is disposed, in the embodiments illustrated in FIGS. 6A and 6B, substantially diametrically centrally on the operating instrument 16. In these embodiments, the substantially central channel 22 has dimensions sufficient for accepting an identifier or scope suitable for visualizing items of interest, such as tissues, vessels and the like, during performance of an operation. Some embodiments include at least one channel provided for fluid movement, such as suction, irrigation and the like, through the operating instrument 16. In the embodiment illustrated in FIG. 6A, there are two fluid movement channels 21 for conveying fluid through the operating instrument 16. In one embodiment, one of the channels 21 can be used for suction while the other is used for irrigation. Connectors 19, such as Luer lock connectors or the like, are located at proximal ends of the channels 21 to facilitate connection of the channels 21 with suitable sources of suction and irrigation.

A distal end of another embodiment of the operating instrument 16 is shown in FIG. 6B. This embodiment is substantially similar to the embodiment shown in FIG. 6A except the differences specified herein. In this embodiment, the substantially central channel 22 has dimensions sufficient for accepting an ultrasound probe suitable for identifying items of interest, such as tissues, vessels and the like, during performance of an operation. An example of a suitable ultrasound probe is a currently available vaginal probe transducer commonly used with pelvic ultrasound procedures. There are three channels that pass through an axial length of the operating instrument 16. The two operating channels 20A and 20B are located adjacent outer edges of the operating instrument 16.

It is to be appreciated that numerous variations of the operating instrument 16 are possible. For example, the operating instrument 16 may include only a central channel 22. In this embodiment, the central channel 22 may be used only to identify the presacral vessels. Fixation of the graft 24 to the sacrum or presacral fascia can be performed laparoscopically. In another embodiment, the operating instrument 16 may have only one operating channel 20. In this embodiment, only one fixation device is utilized. This embodiment may be appropriate if a bone anchor is utilized as only one bone anchor may be sufficient to hold the graft 24 in place.

Any suitable materials, such as polymers, metals and the like, may comprise the introducer sleeve 11, the dissecting instrument 12 and the operating instrument 16 as long as the materials are suitably rigid and are able to be sterilized. The introducer sleeve 11, the dissecting instrument 12 and the operating instrument 16 may be reusable or may be single-use, disposable items.

While the operating instrument 16 described in detail herein provides a means of delivering the graft 24 through a vaginal incision and presenting a sacral end of the graft 24 to the presacral area for fixation, there are other means for delivering and presenting the graft 24. For example, the graft 24 may be disposed between the introducer sleeve 11 and the operating instrument 16. In this instance, the operating instrument 16 does not include a recess 17. The sacral end of the graft 24 could be located at the distal end of the operating channel 20 and tucked into the graft chamber 23. The graft 24 is retained in the graft chamber 23 until the graft 24 is secured to the sacrum. Deployment of the fixation device would remove the graft 24 from the graft chamber 23 as the fixation device fixes the graft 24 to the sacrum or presacral fascia.

With construction of the introducer sleeve 11, dissecting instrument 12 and operating instrument 16 being described, now a method of use of the introducer sleeve 11, dissecting instrument 12 and operating instrument 16 will be discussed. For the sake of clarity of understanding, the method of use will be specifically related to vaginal fixation. However, the introducer sleeve 11, dissecting instrument 12 and operating instrument 16 may be used in any suitable operation involving any appropriate tissue, organ or other part of a body.

The dissecting instrument 12 is inserted into the lumen 25. An incision is made in the vagina. The introducer sleeve 11, containing the dissecting instrument 12, is inserted into the vaginal incision. The length of this first incision is sufficient to accommodate the cross-sectional area of the introducer sleeve 11. Space between the vagina and rectum is appropriately dissected and extended retroperitoneally up to the sacrum. Once the introducer sleeve 11 is appropriately located adjacent the sacrum, the dissecting instrument 12 is removed from the lumen 25 of the introducer sleeve 11.

Before insertion of the operating instrument 13 into the lumen 25, the graft 24 that will be used in creating a bridge of support between the vagina and sacrum is loaded into the graft chamber 23. If the particular embodiment of operating instrument 16 used includes a separable portion 35 and a rod 38, the separable portion 35 is removed from the main body 36 of the operating instrument 16. The graft 24 is appropriately applied to the rod 38 and the rod 38 is appropriately connected with the mounts 37A and 37B. The separable portion 35 is connected with the main body 36 of the operating instrument 16. If the particular embodiment of the operating instrument 16 includes a recess 17, the sacral end of this graft 24 (the end that will be attached to the sacrum) is disposed on the graft supporting platform 32 of the recess 17 on the operating instrument 16. In any embodiment, a portion of the graft 24 extends over distal ends of the operating channels 20A and 20B. The distal end of the operating instrument 16 is positioned for insertion into the lumen 25 of the introducer sleeve 11. This arrangement is shown in FIG. 8.

The distal end of the operating instrument 16 is inserted into the introducer sleeve 11 until the distal end of the operating instrument 16 is substantially flush with the distal end 27 of the introducer sleeve 11. Contact between the surface 33 of the flange 18 and the proximal end 26 of the introducer sleeve 11 restricts longitudinal movement of the operating instrument 16 through the introducer sleeve 11. In one method of use, the fixation devices are inserted into the operating channels 20A and 20B.

A scope or an ultrasound probe is inserted into the central channel 22. The scope or the ultrasound probe is used to identify the middle sacral vessels. Any suitable, commercially available scope may be used. An exemplary scope has an outer diameter of about 5 mm so, if this scope is used, the central channel 22 should have an inner diameter of at least about 5 mm. If the fixation devices were not previously inserted into the operating channels 20A and 20B, the fixation devices are inserted into the operating channels 20A and 20B at this time. The fixation devices may be extended through the operating channels 20A and 20B beyond the distal end of the operating instrument 16.

As the fixation devices are extended, distal ends of the fixation devices move a portion of the graft 24 that extends across the operating channels 20A and 20B. When a fixation device comes in contact with the sacrum, it may be activated to fix a portion of the graft 24 to the sacrum or the presacral fascia at points safely removed from the vessels. If the operating instrument 16 includes the operating channel 20C, the fixation device can be moved laterally during fixation of the graft 24. This process may be repeated as many times as desired in order to establish a sufficiently strong fixation between the graft 24 and the sacrum. Fixation locations are often offset by a distance of about 0.5 cm. As graft 24 fixation proceeds, portions of the graft 24 are moved from the recess 17, the graft chamber 23 and, depending on the embodiment of operating instrument 16 used, the rod 38. As two fixation devices may be arranged in the operating channels 20A and 20B, both fixation devices may be activated substantially simultaneously, although this is not necessary. The operative instrument 16 may be shifted to permit orientation of successive pairs of activations of the fixation devices to be slightly offset or lower than the preceding pair of activations. In this manner, the graft 24 can be fixed at progressively lower and lower locations on the sacrum.

When graft 24 fixation has been accomplished to the satisfaction of the operating surgeon, the operating instrument 16 and introducer sleeve 11 are withdrawn. As withdrawal occurs, the graft 24 is removed from the graft chamber 23. Upon complete removal of the operating instrument 16 and the introducer sleeve 11 from the vagina, the graft 24 remains in the operative field with one end of the graft 24 being fixed to the sacrum while the other end of the graft 24 extends out of the vaginal incision. Excess portions of the graft 24 are trimmed and remaining portions of the graft 24 are fixed to outer surfaces of the vagina using standard suture techniques.

In a related method, a suitable second incision may be made in the anterior vagina and a space created between the bladder and vagina as far as the vaginal apex. The first and second incisions may be joined around the apex. Then, a separate piece of graft material may then be attached to the graft 24 fixed to the sacrum and then attached to the outer surface of the anterior vagina using standard suture techniques.

What is claimed is:

1. An apparatus for suspending an organ within a body, the apparatus comprising;
   (a) a sleeve having a lumen;
   (b) a dissecting instrument being slidably located within the lumen, the dissecting instrument including a channel useful for hydrodissection;
   (c) an operating instrument being slidably located within the lumen, the operating instrument including a graft chamber for conveying a graft for fixation between the organ and the body, the operating instrument including at least one operating channel accepting a fixation device configured to fix the graft within the body, the graft chamber being disposed apart from the operating channel, the operating instrument includes at least one mount that rotatably bears a rod configured to receive the graft, the rod being offset from a longitudinal axis of the operating instrument, the at least one mount being disposed within the graft chamber.

2. The apparatus as defined in claim 1 wherein the sleeve includes a proximal end and the dissecting instrument includes a flange, and wherein contact between the proximal end and the flange restricts longitudinal movement of the dissecting instrument in the lumen of the sleeve.

3. The apparatus as defined in claim 1 wherein the operating instrument includes a recess for accepting a portion of the graft, wherein the recess is located with respect to the graft chamber such that a portion of the graft extends across the at least one operating channel.

4. The apparatus as defined in claim 1 wherein the operating instrument includes a flange and the sleeve includes a proximal end, and wherein contact between the proximal end an the flange restricts longitudinal movement of the operating instrument in the lumen of the sleeve.

5. The apparatus as defined in claim 1 wherein the operating instrument includes a central channel, the central channel having dimensions sufficient to accept at least one of a scope and an ultrasonic probe.

6. The apparatus as defined in claim 1 wherein the operating instrument includes at least one fluid movement channel for conveying fluid through the operating instrument.

7. The apparatus as defined in claim 1 wherein the dissecting instrument has a distal end, and wherein the distal end has a configuration that facilitates dissection.

8. The apparatus as defined in claim 1 wherein the sleeve, the dissecting instrument and the operating instrument have substantially similarly shaped latitudinal cross sections.

9. The apparatus as defined in claim 1 wherein the sleeve includes a pocket that accommodates the graft.

10. The apparatus as defined in claim 1 wherein the operating instrument includes a separable portion that is removable to facilitate access to the graft chamber.

11. The apparatus as defined in claim 1 wherein the rod is disposed perpendicular to the longitudinal axis of the operating instrument.

12. The apparatus as defined in claim 1 wherein the operating instrument further comprises at least one member that suitably adjusts movement of the graft from the rod.

13. The apparatus as defined in claim 1 wherein the organ is a vagina and the body is at least one of a sacrum and presacral fascia.

14. The apparatus of claim 1 wherein the operating instrument comprises at least two operating channels both operating channels being configured to accept a fixation device.

15. The apparatus of claim 1 wherein the at least one operating channel has a substantially elliptical latitudinal cross section.

16. An apparatus for suspending an organ within a body, the apparatus comprising;
(a) a sleeve having a lumen;
(b) an operating instrument being slidably located within the lumen, the operating instrument including a graft chamber for conveying a graft for fixation between the organ and the body, and the operating instrument including at least one operating channel accepting a fixation device configured to fix the graft within the body, the graft chamber being disposed apart from the operating channel, the operating instrument includes at least one mount that rotatably bears a rod configured to receive the graft, the rod being offset from a longitudinal axis of the graft chamber.

17. The apparatus as defined in claim 16 wherein the operating instrument includes a recess for accepting a portion of the graft, wherein the recess is located with respect to the graft chamber such that a portion of the graft extends across the at least one operating channel.

18. The apparatus as defined in claim 16 wherein the operating instrument includes a flange and the sleeve includes a proximal end, and wherein contact between the proximal end and the flange restricts longitudinal movement of the operating instrument in the lumen of the sleeve.

19. The apparatus as defined in claim 16 wherein the operating instrument includes a central channel, the central channel having dimensions sufficient to accept at least one of a scope and an ultrasonic probe.

20. The apparatus as defined in claim 16 wherein the operating instrument includes at least one fluid movement channel for conveying fluid through the operating instrument.

21. The apparatus as defined in claim 16 wherein the sleeve and the operating instrument have substantially similarly shaped latitudinal cross sections.

22. The apparatus as defined in claim 16 wherein the sleeve includes a pocket that accommodates the graft.

23. The apparatus as defined in claim 16 wherein the operating instrument includes a separable portion that is removable to facilitate access to the graft chamber.

24. The apparatus as defined in claim 16 wherein the rod is disposed perpendicular to the longitudinal axis of the operating instrument.

25. The apparatus as defined in claim 16 wherein the operating instrument further comprises at least one member that suitably adjusts movement of the graft from the rod.

26. The apparatus as defined in claim 16 wherein the organ is a vagina and the body is at least one of a sacrum and presacral fascia.

27. The apparatus of claim 16 wherein the operating instrument comprises at least two operating channels both being configured to accept a fixation device.

28. The apparatus of claim 16 wherein the at least one operating channel has a substantially elliptical transverse cross section.

29. The apparatus of claim 1, wherein the operating channel is disposed such that the fixation device may pierce the graft.

30. The apparatus of claim 16, wherein the operating channel is disposed such that the fixation device may pierce the graft.

* * * * *